(12) United States Patent
Beeson et al.

(10) Patent No.: US 9,981,994 B2
(45) Date of Patent: May 29, 2018

(54) PYRAZOLE COMPOUNDS, COMPOSITIONS AND METHODS FOR TREATMENT OF DEGENERATIVE DISEASES AND DISORDERS

(71) Applicant: MUSC FOUNDATION FOR RESEARCH DEVELOPMENT, Charleston, SC (US)

(72) Inventors: Craig C. Beeson, Charleston, SC (US); Christopher C. Lindsey, Wadmalaw Island, SC (US); Yuri K. Peterson, Charleston, SC (US); Baerbel Rohrer, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days. days.

(21) Appl. No.: 15/407,748

(22) Filed: Jan. 17, 2017

(65) Prior Publication Data
US 2017/0121353 A1   May 4, 2017

Related U.S. Application Data

(62) Division of application No. 14/526,721, filed on Oct. 29, 2014, now Pat. No. 9,556,207, which is a division of application No. 13/798,394, filed on Mar. 13, 2013, now Pat. No. 8,921,401.

(51) Int. Cl.
| | |
|---|---|
| *C07D 403/06* | (2006.01) |
| *C07F 7/08* | (2006.01) |
| *C07D 401/04* | (2006.01) |
| *C07D 401/14* | (2006.01) |

(52) U.S. Cl.
CPC .......... *C07F 7/0814* (2013.01); *C07D 401/04* (2013.01); *C07D 401/14* (2013.01); *C07D 403/06* (2013.01)

(58) Field of Classification Search
CPC ......... C07D 403/06; C07F 7/0814; C07F 7/08
USPC .................. 548/110, 364.7; 514/63, 406
See application file for complete search history.

(56) References Cited

U.S. PATENT DOCUMENTS

| | | | | |
|---|---|---|---|---|
| 5,470,862 A | * | 11/1995 | Lin ................. | C07D 401/06 514/303 |
| 6,204,536 B1 | * | 3/2001 | Maeda et al. ............. | 257/355 |
| 6,274,536 B1 | * | 8/2001 | Nebel et al. .............. | 504/252 |
| 7,544,697 B2 | * | 6/2009 | Hays et al. ............... | 514/293 |
| 2009/0075980 A1 | | 3/2009 | Hays et al. | |

FOREIGN PATENT DOCUMENTS

| | | | |
|---|---|---|---|
| JP | 2005200401 | * | 7/2005 |
| JP | 2006131609 | * | 5/2006 |
| WO | 0157024 A1 | | 8/2001 |
| WO | 2005085205 A1 | | 9/2005 |
| WO | 2011103536 A1 | | 8/2011 |
| WO | 2011119869 | | 9/2011 |
| WO | 2011126903 A2 | | 10/2011 |

OTHER PUBLICATIONS

Katsumata et al I. CA 143: 306305 (2005).*
Katsumata et al. II CA 143; 153367 (2005).*
Bizzi et al. CA 67:98714 (1967).*
Database Registry [Online], Chemical Abstracts Service, Columbus, Ohio, US; Jan. 10, 2013(Jan. 10, 2013), XP002724950, Database accession No. 1416372-78-5.
Database Registry [Online], Chemical Abstracts Service, Columbus, Ohio, US; Jan. 27, 2011(Jan. 27, 2011), XP002724951, Database accession No. 1260841-08-4.
Database Registry [Online], Chemical Abstracts Service, Columbus, Ohio, US; May 11, 2008(May 11, 2008), XP002724952, Database accession No. 1020238-67-8.
Database Registry [Online], Chemical Abstracts Service, Columbus, Ohio, US; Apr. 18, 1996(Apr. 18, 1996), XP002724953, atabase accession No. 175277-04-0.
Database Registry [Online], Chemical Abstracts Service, Columbus, Ohio, US; Nov. 18, 2003(Nov. 18, 2003), XP002724954, Database accession No. 618070-58-9.
Database Registry [Online], Chemical Abstracts Service, Columbus, Ohio, US; Nov. 18, 2003(Nov. 18, 2003), XP002724955, Database accession No. 618070-59-0.
The International Search Report and Written Opinion, dated Jun. 17, 2014, in the related PCT Appl. No. PCT/US14/25985.
The European Communication, dated Nov. 14, 2016, in the related European Appl. No. 14 720 792.2.
The Australian Examination Report, dated Apr. 7, 2017, in the related Australian Appl. No. 2014244081.

* cited by examiner

*Primary Examiner* — Patricia L Morris

(57) ABSTRACT

Provided herein are compounds of the formula (I):

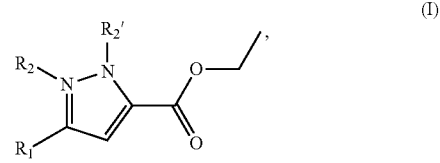

(I)

as well as pharmaceutically acceptable salts thereof, wherein the substituents are as those disclosed in the specification. These compounds, and the pharmaceutical compositions containing them, are useful for the treatment of degenerative diseases and disorders.

7 Claims, No Drawings

PYRAZOLE COMPOUNDS, COMPOSITIONS AND METHODS FOR TREATMENT OF DEGENERATIVE DISEASES AND DISORDERS

This application claims priority to and is a divisional of pending U.S. patent application Ser. No. 14/526,721, filed Oct. 29, 2014, which in turn claims priority to and is a divisional U.S. patent application Ser. No. 13/798,394, filed Mar. 13, 2013 and issued as U.S. Pat. No. 8,921,404, all of which are hereby incorporated by reference in their entireties.

FIELD OF THE INVENTION

The invention is directed to compounds of formula (I):

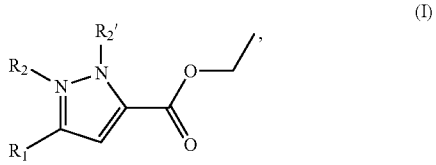

and to pharmaceutical compositions comprising the compounds. The compounds and compositions disclosed herein protect against calcium- and oxidative-stress mediated damage to mitochondrial function and are useful for the treatment of degenerative diseases and disorders.

All documents cited or relied upon below are expressly incorporated herein by reference.

BACKGROUND OF THE INVENTION

Mitochondria are cellular organelles present in most eukaryotic cells. One of their primary functions is oxidative phosphorylation, a process through which energy derived from metabolism of fuels like glucose or fatty acids is converted to ATP, which is then used to drive various energy-requiring biosynthetic reactions and other metabolic activities. Mitochondria have their own genomes, separate from nuclear DNA, comprising rings of DNA with about 16,000 base pairs in human cells. Each mitochondrion may have multiple copies of its genome, and individual cells may have hundreds of mitochondria. In addition to supplying cellular energy, mitochondria are involved in a range of other processes, such as signaling, cellular differentiation, cell death, as well as the control of the cell cycle and cell growth (McBride et al., Curr. Biol., 2006, 16 (14): R551).

As mitochondria produce ATP, they simultaneously yield reactive oxygen species (ROS), which are harmful free radicals that circulate throughout the cell, the mitochondria, and the body, causing more damage. The circulation of ROS leads to the activation of reactive nitrogen compounds, which in turn induce, or activate, genes in the DNA that are associated with many degenerative diseases. The DNA for each mitochondrion (mtDNA) remains unprotected within the membrane of the mitochondrion itself. In comparison to the DNA in the nucleus of the cell (nDNA), mtDNA is easily damaged by free radicals and the ROS that it produces. Freely floating mtDNA lacks protective measures associated with nDNA, and therefore suffers from multiple mutations. It has been estimated that the lack of protective measures results in mutations to mtDNA occurring 10 to 20 times more frequently than mutations to nDNA.

Mitochondrial damage and/or dysfunction contribute to various disease states. Some diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms can be present, depending on the extent to which different tissues are involved.

A fertilized ovum might contain both normal and genetically defective mitochondria. The segregation of defective mitochondria into different tissues during division of this ovum is a stochastic process, as will be the ratio of defective to normal mitochondria within a given tissue or cell (although there can be positive or negative selection for defective mitochondrial genomes during mitochondrial turnover within cells). Thus, a variety of different pathologic phenotypes can emerge out of a particular point mutation in mitochondrial DNA. Conversely, similar phenotypes can emerge from mutations or deletions affecting different genes within mitochondrial DNA. Clinical symptoms in congenital mitochondrial diseases often manifest in postmitotic tissues with high energy demands like brain, muscle, optic nerve, and myocardium, but other tissues including endocrine glands, liver, gastrointestinal tract, kidney, and hematopoietic tissue are also involved, again depending in part on the segregation of mitochondria during development, and on the dynamics of mitochondrial turnover over time.

In addition to congenital disorders involving inherited defective mitochondria, acquired mitochondrial damage and/or dysfunction contribute to diseases, particularly neurodegenerative disorders associated with aging like Parkinson's, Alzheimer's, Huntington's Diseases. The incidence of somatic mutations in mitochondrial DNA rises exponentially with age; and diminished respiratory chain activity is found universally in aging people. Mitochondrial dysfunction is also implicated in excitotoxic neuronal injury, such as that associated with seizures or ischemia.

Other pathologies with etiology involving mitochondrial damage and/or dysfunction include schizophrenia, bipolar disorder, dementia, epilepsy, stroke, cardiovascular disease, retinal degenerative disease (e.g., age-related macular degeneration, Stargardt's disease, glaucoma, retinitis pigmentosa, and optic nerve degeneration), and diabetes mellitus. A common thread thought to link these seemingly-unrelated conditions is cellular damage causing oxidative stress. Oxidative stress is caused by an imbalance between the production of reactive oxygen and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA.

Mitochondrial damage and/or dysfunction particularly contribute to degenerative disesaes. Degenerative diseases are diseases in which the function or structure of the affected tissues or organs will progressively deteriorate over time. Some examples of degenerative diseases are retinal degenerative disease, e.g., age-related macular degeneration, Stargardt's disease, glaucoma, retinitis pigmentosa, and optic nerve degeneration; amyotrophic lateral sclerosis (ALS), e.g., Lou Gehrig's Disease; Alzheimer's disease; Parkinson's Disease; multiple system atrophy; Niemann Pick disease; atherosclerosis; progressive supranuclear palsy; cancer; Tay-Sachs disease; diabetes; heart disease; keratoconus; inflammatory bowel disease (IBD); prostatitis; osteoarthritis; osteoporosis; rheumatoid arthritis; and Huntington's disease.

Treatment of degenerative diseases involving mitochondrial damage and/or dysfunction has heretofore involved administration of vitamins and cofactors used by particular elements of the mitochondrial respiratory chain. Coenzyme Q (ubiquinone), nicotinamide, riboflavin, carnitine, biotin, and lipoic acid are used in patients with occasional benefit, especially in disorders directly stemming from primary deficiencies of one of these cofactors. However, while useful in isolated cases, no such metabolic cofactors or vitamins have been shown to have general utility in clinical practice in treating degenerative diseases involving mitochondrial damage and/or dysfunction.

Therefore, a need exists for new drug therapies for the treatment of subjects suffering from or susceptible to the above disorders or conditions associated with mitochondrial damage and/or dysfunction. In particular, a need exists for new drugs having one or more improved properties (such as safety profile, efficacy or physical properties) relative to those currently available.

SUMMARY OF THE INVENTION

The present invention is directed to compounds of formula I:

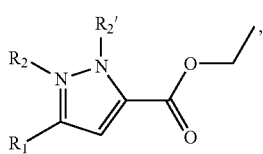

(I)

wherein:
$R_1$ is lower alkyl, trimethylsilyl or pyridinyl;
one of $R_2$ or $R_2'$ is absent and the other is —$CH_2R_3$ or —$CH_2C(O)R_3$; and
$R_3$ is pyridinyl, 1H-indol-3-yl, unsubstituted phenyl or phenyl mono-, bi- or tri-substituted independently with alkoxy, or a pharmaceutically acceptable salt thereof.

The present invention is also directed to pharmaceutical compositions containing the above compounds, method of using the compounds and to methods of treating degenerative diseases and disorders.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a bromine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In one embodiment of the invention, provided is a compound of formula (I):

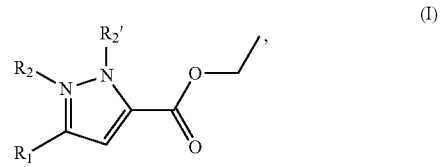

wherein:
$R_1$ is lower alkyl, trimethylsilyl or pyridinyl;
one of $R_2$ or $R_{2'}$ is absent and the other is —$CH_2R_3$ or —$CH_2C(O)R_3$; and
$R_3$ is pyridinyl, 1H-indol-3-yl, unsubstituted phenyl or phenyl mono-, bi- or tri-substituted independently with alkoxy, or a pharmaceutically acceptable salt thereof.

In another embodiment of the invention, provided is a compound according to formula (I), wherein $R_1$ is lower alkyl.

In another embodiment of the invention, provided is a compound according to formula (I), wherein $R_1$ is trimethylsilyl.

In another embodiment of the invention, provided is a compound according to formula (I), wherein $R_1$ is pyridinyl.

In another embodiment of the invention, provided is a compound according to formula (I), wherein one of $R_2$ or $R_{2'}$ is absent and the other is —$CH_2R_3$.

In another embodiment of the invention, provided is a compound according to formula (I), wherein one of $R_2$ or $R_{2'}$ is absent and the other is —$CH_2C(O)R_3$.

In another embodiment of the invention, provided is a compound according to formula (I), wherein $R_3$ is pyridinyl.

In another embodiment of the invention, provided is a compound according to formula (I), wherein $R_3$ is 1H-indol-3-yl.

In another embodiment of the invention, provided is a compound according to formula (I), wherein $R_3$ is phenyl mono-substituted with methoxy.

In another embodiment of the invention, provided is a compound according to formula (I), wherein $R_3$ is phenyl bi-substituted with methoxy.

In another embodiment of the invention, provided is a compound according to formula (I), wherein $R_3$ is phenyl tri-substituted with methoxy.

In another embodiment of the invention, provided is a compound according to formula (I), wherein $R_2$ is absent, $R_{2'}$ is —$CH_2C(O)R_3$ and $R_3$ is phenyl bi-substituted with methoxy.

In another embodiment of the invention, provided is a compound according to formula (I), wherein the compound is:
Ethyl 1-(2-(2,4-dimethoxyphenyl)-2-oxoethyl)-3-(pyridin-2-yl)-1H-pyrazole-5-carboxylate;
Ethyl 1-(2-(2,4-dimethoxyphenyl)-2-oxoethyl)-5-(pyridin-2-yl)-1H-pyrazole-3-carboxylate;
Ethyl 1-(2-(2,5-dimethoxyphenyl)-2-oxoethyl)-3-(pyridin-3-yl)-1H-pyrazole-5-carboxylate;
Ethyl 1-(2-(2,4-dimethoxyphenyl)-2-oxoethyl)-3-(trimethylsilyl)-1H-pyrazole-5-carboxylate;
Ethyl 1-(2-(2,5-dimethoxyphenyl)-2-oxoethyl)-3-(trimethylsilyl)-1H-pyrazole-5-carboxylate;
Ethyl 3-(pyridin-2-yl)-1-(pyridin-3-ylmethyl)-1H-pyrazole-5-carboxylate;
Ethyl 1-(3,4,5-trimethoxybenzyl)-3-(trimethylsilyl)-1H-pyrazole-5-carboxylate;
Ethyl 1-(2-(2,4-dimethoxyphenyl)-2-oxoethyl)-3-(pyridin-3-yl)-1H-pyrazole-5-carboxylate;
Ethyl 1-(2-oxo-2-(pyridin-3-yl)ethyl)-5-(trimethylsilyl)-1H-pyrazole-3-carboxylate;
Ethyl 1-(2-oxo-2-(pyridin-3-yl)ethyl)-3-(trimethylsilyl)-1H-pyrazole-5-carboxylate;
Ethyl 1-(2-(2,5-dimethoxyphenyl)-2-oxoethyl)-3-(pyridin-2-yl)-1H-pyrazole-5-carboxylate; or
Ethyl 1-((1H-indol-3-methyl)-3-isopropyl-1H-pyrazole-5-carboxylate.

In a further embodiment of the invention, provided is a pharmaceutical composition, comprising a therapeutically effective amount of a compound according to formula (I) or a pharmaceutically acceptable salt thereof and a pharmaceutically acceptable carrier.

In a further embodiment of the invention, provided is a method for treating a degenerative disease or disorder, comprising the step of administering a therapeutically effective amount of a compound according to formula (I) or a pharmaceutically acceptable salt thereof and a pharmaceutically acceptable carrier to a patient in need thereof. The degenerative diseases and disorders include, for example, retinitis pigmentosa.

In another embodiment of the invention, provided is a method of treating a retinal degenerative disease in a subject in need thereof, comprising administering to said subject a therapeutically effective amount of a compound or a pharmaceutically acceptable salt thereof according to formula (I).

In a yet further embodiment of the invention, provided is a method for preventing calcium-induced or oxidant-induced mitochondrial damage preventing or loss of mitochondrial respiratory capacity in a cell susceptible thereof wherein the calcium-induced or oxidant-induced mitochondrial damage or loss of mitochondrial respiratory capacity comprises excess of cGMP that increases the number of cGMP-gated cation channels in an open configuration, allowing an influx of Ca2+ into the cell, said method comprising contacting the cell with an effective amount of a compound or a pharmaceutically acceptable salt thereof according to formula (I).

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

The compounds of formula I can be prepared according to the following scheme:

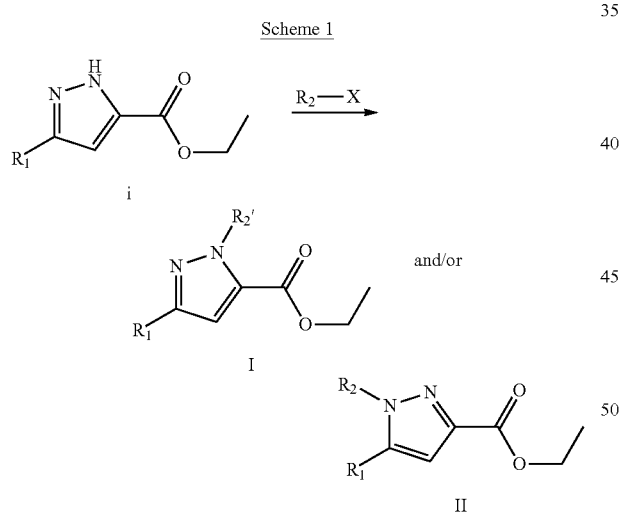

As seen in Scheme 1, compounds of formula I and II (collectively "formula (I)") may be made using intermediate i. Intermediate i may be made from reacting an acetylene where $R_1$ can be, for example, aryl, phenyl, 2-pyridyl, or 3-pyridyl, methyl, tert-butyl, trimethyl silyl, trialkyl silyl, dialkylphenylsilyl, diphenylalkylsilyl, or triphenylsilyl with the appropriately commercially available diazoethyl acetate (purchased from Aldrich) at the appropriate temperature (such as 95° C.) for the appropriate time (such as 24 hours) (Cheung, K. M. J.; Reynisson, J.; McDonald, E. Tetrahedron Lett. 2010, 51 5915-5918). Formation of compounds of formula I may then be made by reacting intermediates of formula i with a base such as LiHMDS, KHMDS, NaHMDS, LDA, BuLi, t-BuMgCl, any alkyl lithium, any aryl lithium, any alkyl Grignard, or any aryl Grignard, that may or may not be in the presence of 18-crown-6, or compounds analogous thereto, in a solvent such as DMF, THF, or 1,4 dioxane at the appropriate temperature with any commercially available $R_2$—X to afford compounds of formulation I or II as either a mixture, or exclusive. $R_2$ and $R_{2'}$, independently of each other, may be, for example, benzyl, aryl, aryl keto, 2,4-dimethoxyphenyl)-2-oxoethyl, (2,5-dimethoxyphenyl)-2-oxoethyl, pyridin-3-ylmethyl, 3,4,5-trimethoxybenzyl, 2-oxo-2-(pyridin-3-yl)ethyl, -(1H-indol-3-yl)methyl. X may be any halogen such as chlorine, bromine, or iodine.

The invention will now be further described in the Examples below, which are intended as an illustration only and do not limit the scope of the invention.

EXAMPLES

I. Preparation of Certain Intermediates of the Invention

Ethyl 3-(trimethylsilyl)-1H-pyrazole-5-carboxylate

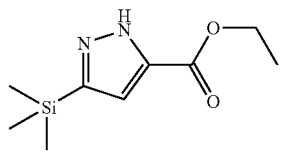

To a flame dried sealed tube equipped with a stir bar that was cooled under argon was added trimethylsilylacetylene (1.0 mL, 9.56 mmol) and ethyldiazoacetate (1.5 mL, 9.6 mmol). The tube was then sealed and heated to 95° C. over night. The next day the reaction was cooled to room temperature and the resulting mixture diluted with hexanes. It was then filtered. The precipitate was then washed with hexanes twice. It was then used without any further purification.

Ethyl 3-(pyridin-2-yl)-1H-pyrazole-5-carboxylate

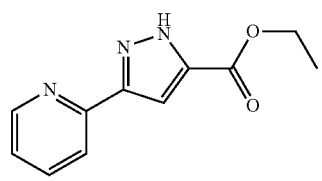 [SMILES: CCOC(=O)c1cc(-c2ccccn2)n[nH]1]

Was prepared in a similar way as ethyl 3-(trimethylsilyl)-1H-pyrazole-5-carboxylate using diazoethyl acetate (Purchased from Aldrich) and 2-ethynyl-pyridine (Purchased from Aldrich).

Ethyl 3-(pyridin-3-yl)-1H-pyrazole-5-carboxylate

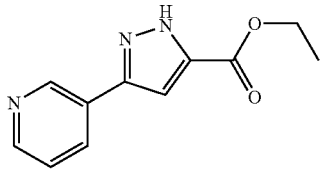 [SMILES: CCOC(=O)c1cc(-c2cccnc2)n[nH]1]

Was prepared in a similar way to ethyl 3-(trimethylsilyl)-1H-pyrazole-5-carboxylate using diazoethyl acetate (Purchased from Aldrich) and 2-ethynyl-pyridine (Purchased from Aldrich)

1-Benzoyl-1H-indol-3-yl)methyl benzoate

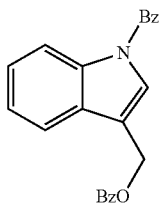

To an oven dried flask that cooled under argon was added the (1H-indol-3-yl)methanol (1.0 grams, 6.8 mmol, 0.1M in dry dichloromethane, purchased from Fisher Scientific, stored over 4 angstrom molecular sieves) and DMAP (0.083 grams, 0.68 mmol). While stirring at 0° C., triethyl amine (2.0 mL, 14.3 mmol, purchased from Fisher Scientific) was added followed by benzoyl chloride (0.96 mL, 8.2 mmol, purchased from Fisher Scientific). Once the reaction was complete it was diluted with water, and the organic layer removed. The aqueous layer was then washed with dichloromethane twice and the organic material combined. The organic material was dried with sodium sulfate, filtered, and concentrated. Purification using a Teledyne ISCO on silica support (hexanes/ethyl acetate gradient) afforded the desired 1-benzoyl-1H-indol-3-yl)methyl benzoate. 42% yield. 1H-NMR δ 8.42 (d, 1H), 8.02 (dd, 2H), 7.76 (m, 3H), 7.62 (dd, 1H), 7.54 (m, 3H), 7.47-7.37 (m, 5H), 5.50 (s, 2H).

Ethyl 3-isopropyl-1H-pyrazole-5-carboxylate

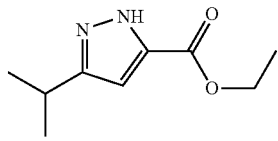

To a clean round bottom flask equipped with a stir bar, Dean-Stark trap, and reflux condenser was added 3-isopropyl-1H-pyrazole-5-carboxylic acid (1 gram, 6.49 mmol, purchased from Fisher Scientific). 30 mL of ethanol (95%, purchased from Fisher Scientific) was added followed by 30 mL of benzene. 43 μL of acetyl chloride was then added and the solution refluxed over the three days. The solvent was then removed using a Buchi rotoevaporator. The residue was then taken up in ethyl acetate and washed with NaHCO3 (saturated). It was then dried with sodium sulfate, filtered and concentrated. Purification using a Teledyne ISCO silica chromatography (hexanes/ethyl acetate gradient) afforded the desired ester. Yield, 85% 1H-NMR δ 6.7 (s, 1H), 5.1 (bs, NH), 4.41 (q, 2H), 3.13 (septet, 1H), 1.38 (t, 3H), 1.33 (d, 6H).

II. Preparation of Certain Embodiments of the Invention

Examples 1 and 2

Ethyl 1-(2-(2,4-dimethoxyphenyl)-2-oxoethyl)-3-(pyridin-2-yl)-1H-pyrazole-5-carboxylate and Ethyl 1-(2-(2,4-dimethoxyphenyl)-2-oxoethyl)-5-(pyridin-2-yl)-1H-pyrazole-3-carboxylate

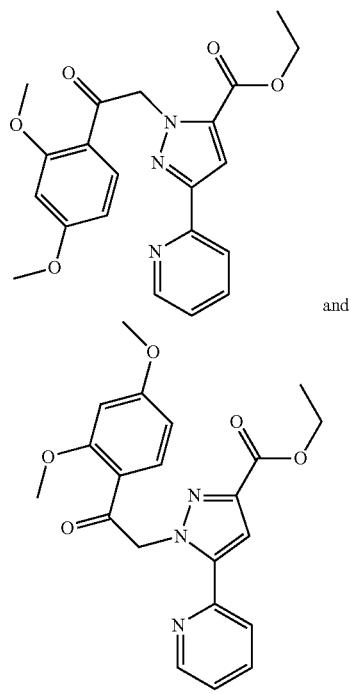

and

To an oven dried flask equipped with a stir bar cooled under argon was added ethyl 3-(pyridin-2-yl)-1H-pyrazole-5-carboxylate (0.03 grams, 0.14 mmol, 0.1M in 1,4 dioxane (anhydrous Sure Seal, purchased from Aldrich)). While stirring at room temperature, a solution of KHMDS (0.17 mL, 0.15 mmol, 0.87M in toluene, purchased from Fisher Scientific) was added slowly. In a separate oven dried flask cooled under argon was added 2-bromo-1-(2,4-dimethoxyphenyl)ethanone (0.04 grams, 0.154 mmol, 0.1M in 1,4 dioxane (anhydrous Sure Seal, purchased from Aldrich)).

After stirring for one hour at room temperature the solution of dimethoxyphenylethanone was added to the ethyl 3-(pyridin-2-yl)-1H-pyrazole-5-carboxylate and the reaction continued to stir at room temperature over night. The next day, the reaction was diluted with 0.1M HCl and ethyl acetate. The organic material was extracted. The aqueous layer was salted out with sodium chloride and washed twice with ethyl acetate. The combined organic material was then dried with sodium sulfate, filtered and concentrated. Purification using a Teledyne ISCO on a silica support (hexanes, ethyl acetate gradient) affords the two regioisomers in a 1:1 ratio. Further purification can be done using a Teledyne ISCO C18 reverse phase column using water with 0.1% formic acid, acetonitrile gradient. Combined yield, 60%. 1-(2-(2,4-dimethoxyphenyl)-2-oxoethyl)-3-(pyridin-2-yl)-1H-pyrazole-5-carboxylate 1H-NMR □ 8.34 (ddd, 1H), 7.81 (d, 1H), 7.69 (m, 2H), 7.29 (s, 1H), 7.14 (m, 1H), 6.54 (dd, 1H), 6.51 (d, 1H), 6.23 (s, 2H), 4.4 (q, 2H), 3.97 (s, 3H), 3.88 (s, 3H), 1.43 (t, 3H). Calculated mass for C21H21N3O5, 395.15, observed, 396.2 (M+1).

1-(2-(2,4-dimethoxyphenyl)-2-oxoethyl)-5-(pyridine-2-yl)-1H-pyrazole-3-carboxylate. 1H-NMR δ 8.33 (dd, 1H), 7.81 (d, 1H), 7.69 (m, 2H), 7.28 (s, 1H), 7.14 (t, 1H), 6.54 (dd, 1H), 6.50 (d, 1H), 6.22 (s, 2H), 4.44 (d, 2H), 3.96 (s, 3H), 3.88 (s, 3H), 1.42 (t, 3H). Calculated mass for C21H21N3O5, 395.15, observed, 418.1 (M+Na).

Example 3

Ethyl 1-(2-(2,5-dimethoxyphenyl)-2-oxoethyl)-3-(pyridin-3-yl)-1H-pyrazole-5-carboxylate

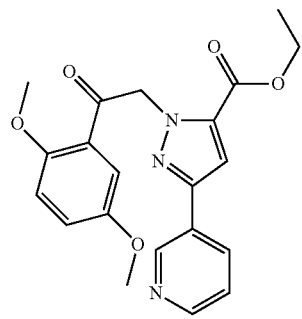 [SMILES: CCOC(=O)c1cc(-c2cccnc2)nn1CC(=O)c1cc(OC)ccc1OC]

To a flame dried flask equipped with a stirbar cooled under argon was added ethyl 3-(pyridin-3-yl)-1H-pyrazole-5-carboxylate (0.02 grams, 0.092 mmol, 0.1M in THF). While stirring at room temperature NaH (0.0055 grams, 1.8 mmol, 60% in mineral oil, purchase from Aldrich) was added. After fifteen minutes 2-bromo-1-(2,5-dimethoxyphenyl)ethanone (0.047 grams, 0.14 mmol, purchased from Aldrich) was added as a solid. The reaction was stirred overnight. The next day, the reaction was quenched with 0.1M HCl and the organic material extracted using ethyl acetate. The aqueous layer was salted out using sodium chloride and washed twice with ethyl acetate. The combined organic material was then dried with sodium sulfate, filtered, and concentrated. Purification was done on preparative thin layer chromatography using hexanes/ethyl acetate (1:2) to afford the desired compound. Yield, 10%. 1H-NMR δ 9.07 (bs, 1H), 8.58 (bs, 1H), 8.13 (d, 1H), 7.47 (d, 1H), 7.31 (bs, 1H), 7.29 (s, 1H), 7.14 (dd, 1H), 7.00 (d, 1H), 6.03 (s, 2H), 4.32 (q, 2H), 3.99 (s, 3H), 3.79 (s, 3H), 1.35 (t, 3H). Calculated mass for C21H21N3O5, 395.15, observed, 396.3 (M+1).

Example 4

Ethyl 1-(2-(2,4-dimethoxyphenyl)-2-oxoethyl)-3-(trimethylsilyl)-1H-pyrazole-5-carboxylate

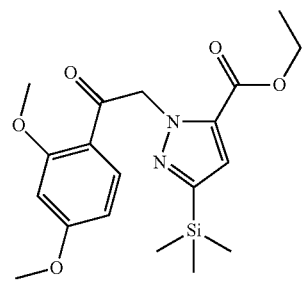 [SMILES: CCOC(=O)c1cc([Si](C)(C)C)nn1CC(=O)c1ccc(OC)cc1OC]

This compound was prepared in a similar method to ethyl 1-(2-(2,5-dimethoxyphenyl)-2-oxoethyl)-3-(pyridin-3-yl)-1H-pyrazole-5-carboxylate using ethyl 3-(trimethylisilyl)-1H-pyrazole-5-carboxylate and 2-bromo-1-(2,4-dimethoxyphenyl)ethanone (purchased from Aldrich). 1H-NMR δ 9.92 (d, 1H), 7.02 (s, 1H), 6.57 (dd, 1H), 6.51 (d, 1H), 5.67 (s, 2H), 4.39 (quartet, 2H), 3.98 (s, 3H), 3.89 (s, 3H), 1.38 (t, 3H), 0.27 (s, 9H).

Example 5

Ethyl 1-(2-(2,5-dimethoxyphenyl)-2-oxoethyl)-3-(trimethylsilyl)-1H-pyrazole-5-carboxylate

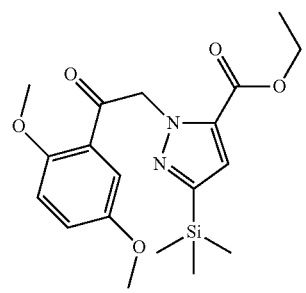 [SMILES: CCOC(=O)c1cc([Si](C)(C)C)nn1CC(=O)c1cc(OC)ccc1OC]

This compound was prepared in a similar method to ethyl 1-(2-(2,5-dimethoxyphenyl)-2-oxoethyl)-3-(pyridin-3-yl)-1H-pyrazole-5-carboxylate using ethyl 3-(trimethylisilyl)-1H-pyrazole-5-carboxylate and 2-bromo-1-(2,5-dimethoxypheny)ethanone (Purchased from Aldrich). 1H-NMR δ 7.40 (d, 1H), 7.12 (dd, 1H), 7.02 (dd, 1H), 6.96 (d, 1H), 5.72 (s, 2H), 4.40 (q, 2H), 3.96 (s, 3H), 3.78 (s, 3H), 1.39 (t, 3H), 0.28 (s, 9H).

Example 6

Ethyl 3-(pyridin-2-yl)-1-(pyridin-3-ylmethyl)-1H-pyrazole-5-carboxylate

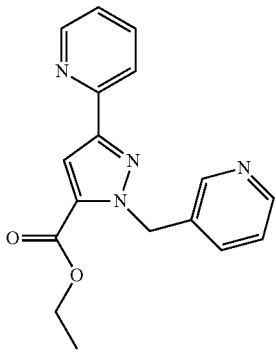 [SMILES: CCOC(=O)c1cc(-c2ccccn2)nn1Cc1cccnc1]

To a flame dried flask equipped with a stir bar cooled under argon was added ethyl 3-(pyridin-3-yl)-1H-pyrazole-5-carboxylate (0.02 grams, 0.092 mmol), 3-bromo-methylene-pyridine.HBr (0.0466 grams, 0.18 mmol, purchased from Aldrich) and 1 mL of THF (anhydrous, Sure Seal purchased from Aldrich). While stirring at room temperature sodium hydride (0.011 grams, 0.28 mmol, 60% in mineral oil, purchased from Aldrich), was added and the reaction continued to stir over night at room temperature. The next day, the reaction was quenched with 0.1M HCl, and the organic material extracted using ethyl acetate. The aqueous layer was then salted out using sodium chloride, and washed twice with ethyl acetate. The combined organic material was then dried with sodium sulfate, filtered, and concentrated. Purification was done on preparative thin layer chromatography using hexanes/ethyl acetate (1:2) to afford the desired compound. Yield, 9.4%. 1H-NMR δ 8.67 (m, 2H), 8.56 (m, 1H), 8.00 (d, 1H), 7.80-7.72 (m, 2H), 7.56 (m, 1H), 7.35-7.24 (m, 2H), 5.88 (s, 2H), 4.34 (q, 2H), 1.36 (t, 3H).

Example 7

Ethyl 1-(3,4,5-trimethoxybenzyl)-3-(trimethylsilyl)-1H-pyrazole-5-carboxylate

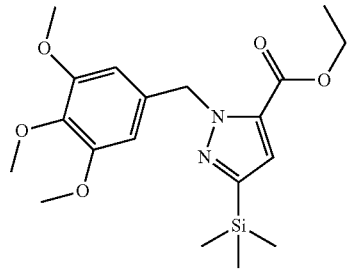 [SMILES: CCOC(=O)c1cc([Si](C)(C)C)nn1Cc1cc(OC)c(OC)c(OC)c1]

This compound was made in an analogous fashion to ethyl 1-(2-(2,5-dimethoxyphenyl)-2-oxoethyl)-3-(pyridin-3-yl)-1H-pyrazole-5-carboxylate using ethyl 3-(trimethylsilyl)-1H-pyrazole-5-carboxylate and 3,4,5-trimethoxy benzyl chloride (purchased from Aldrich). 1H-NMR δ 6.98 (s, 1H), 6.21 (s, 2H), 5.44 (s, 2H), 4.41 (q, 2H), 3.81 (s, 3H), 3.76 (s, 6H), 1.40 (t, 3H), 0.22 (s, 9). Calculated mass for C19H28N2O5Si, 392.18, observed, 393.0 (M+1), 415.1 (M+Na).

Example 8

Ethyl 1-(2-(2,4-dimethoxyphenyl)-2-oxoethyl)-3-(pyridin-3-yl)-1H-pyrazole-5-carboxylate

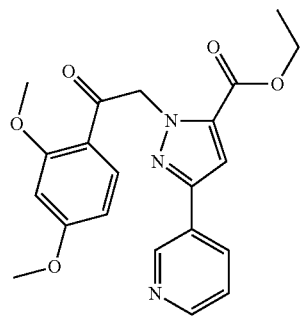 [SMILES: CCOC(=O)c1cc(-c2cccnc2)nn1CC(=O)c1ccc(OC)cc1OC]

This compound was made in an analogous fashion to ethyl 1-(2-(2,5-dimethoxyphenyl)-2-oxoethyl)-3-(pyridin-3-yl)-1H-pyrazole-5-carboxylate using ethyl 3-(pyridin-3-yl)-1H-pyrazole-5-carboxylate and 2-bromo-1-(2,4-dimethoxypheny)ethanone (purchased from Aldrich). 1H-NMR δ 9.08 (s, 1H), 8.58 (d, 1H), 8.14 (d, 1H), 8.00 (d, 1H), 7.33 (m, 1-1), 7.27 (s, 1H), 6.58 (dd, 1H), 6.49 (d, 1H), 5.98 (s, 2H), 4.31 (q, 2H), 4.00, (s, 3H), 3.88 (s, 3H), 1.34 (t, 3H). Calculated mass for C21H21N3O5, 395.15, observed, 396.2 (M+1).

Example 9

Ethyl 1-(2-oxo-2-(pyridin-3-yl)ethyl)-5-(trimethylsilyl)-1H-pyrazole-3-carboxylate

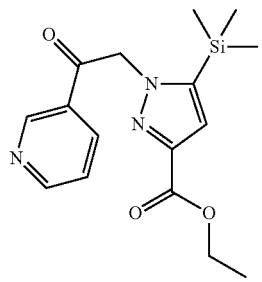 [SMILES: CCOC(=O)c1cc([Si](C)(C)C)n(CC(=O)c2cccnc2)n1]

This compound was made in an analogous fashion to ethyl 1-(2-(2,5-dimethoxyphenyl)-2-oxoethyl)-3-(pyridin-3-yl)-1H-pyrazole-5-carboxylate using ethyl 3-(trimethylsilyl)-1H-pyrazole-5-carboxylate and 2-bromo-1-(pyridin-3-ethanone.HBr (purchased from Aldrich). 1H-NMR δ 9.17 (d, 1H), 8.88 (dd, 1H), 8.24 (ddd, 1), 7.50 (td, 1H), 7.03 (s, 1H), 5.73 (s, 2H), 4.40 (q, 2H), 1.39 (t, 3H), 0.28 (s, 9H). Calculated mass for C16H21N3O3Si, 331.14, observed, 332.0 (M+1).

Example 10

Ethyl 1-(2-oxo-2-(pyridin-3-yl)ethyl)-3-(trimethylsilyl)-1H-pyrazole-5-carboxylate

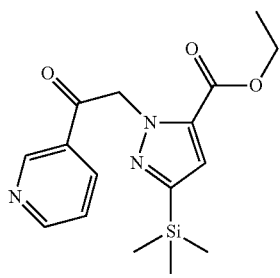 [SMILES: CCOC(=O)c1cc([Si](C)(C)C)nn1CC(=O)c1cccnc1]

This compound was made in an analogous fashion to ethyl 1-(2-(2,5-dimethoxyphenyl)-2-oxoethyl)-3-(pyridin-3-yl)-1H-pyrazole-5-carboxylate using ethyl 3-(trimethylsilyl)-1H-pyrazole-5-carboxylate and 2-bromo-1-(pyridin-3-ethanone.HBr (purchased from Aldrich). 1H-NMR δ 9.20 (d, 1H), 8.84 (dd, 1H), 8.25 (dt, 1H), 7.46 (dd, 1H), 7.07 (s, 1H), 6.05 (s, 2H), 4.26 (q, 2H), 1.31 (t, 3H), 0.32 (s, 9H). Calculated mass for C16H21N3O3Si, 331.14, observed, 332.0 (M+1).

Example 11

Ethyl 1-(2-(2,5-dimethoxyphenyl)-2-oxoethyl)-3-(pyridin-2-yl)-1H-pyrazole-5-carboxylate

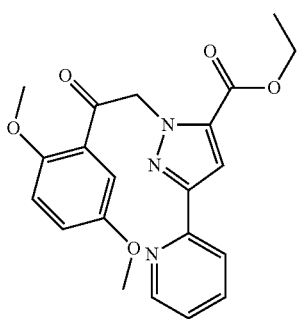 [SMILES: CCOC(=O)c1cc(-c2ccccn2)nn1CC(=O)c1cc(OC)ccc1OC]

This compound was made in an analogous fashion to ethyl 1-(2-(2,5-dimethoxyphenyl)-2-oxoethyl)-3-(pyridin-3-yl)-1H-pyrazole-5-carboxylate using ethyl 3-(trimethylsilyl)-1H-pyrazole-5-carboxylate and 2-bromo-1-(2,5-dimethoxyphenyl)ethanone (purchased from Aldrich). 1H-NMR δ 8.65 (dt, 1H), 7.94 (d, 1H), 7.72 (dd, 1H), 7.57 (s, 1H), 7.47 (d, 1H), 7.22 (dd, 1H), 7.13 (dd, 1H), 6.98 (s, 1H), 6.05 (s, 2H), 4.28 (q, 2H), 3.98 (s, 3H), 3.78 (s, 3H), 1.33 (t, 3H). Calculated mass for C21H21N3O5, 395.15, observed, 396.2 (M+1).

Example 12

Ethyl 1-((1H-indol-3-yl)methyl)-3-isopropyl-1H-pyrazole-5-carboxylate

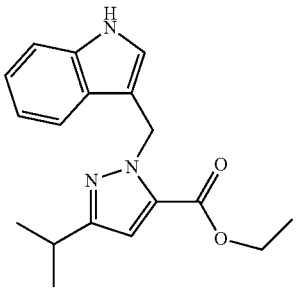 [SMILES: CCOC(=O)c1cc(C(C)C)nn1Cc1c[nH]c2ccccc12]

To an oven dried flask cooled under argon equipped with a stir bar was added ethyl 3-isopropyl-1H-pyrazole-5-carboxylate (0.044 grams, 0.24 mmol, 0.1 in anhydrous 1,4 dioxane). While stirring at room temperature KHMDS (0.3 mL, 0.261 mmol, 0.87M in toluene) was added. After stirring for 45 minutes, a solution of (1-benzoyl-1H-indol-3-yl)methyl benzoate (0.02 grams, 0.056 mmol, in 1.0 mL of anhydrous 1,4 dioxane) was added and the reaction mixture stirred over night. The next day, the reaction was quenched with 0.1M HCl and the organic material extracted with ethyl acetate. The aqueous solution was then salted out using sodium chloride and washed twice with ethyl acetate. The combined organic material was then dried with sodium sulfate, filtered, and concentrated. Purification using a Teledyne ISCO chromatography on silica gel (hexanes/ethyl acetate gradient) followed by a Teledyne ISCO chromatography using C18 reverse phase (water with 0.1% formic acid, acetonitrile gradient) afforded the desired compound. Yield, 63%. 1H NMR δ 8.29 (bs, 1H), 7.58 (d, 1H), 7.36 (d, 1H), 7.20 (t, 1H), 7.11 (t, 1H), 6.96 (s, 1), 6.62 (s, 1H), 5.58 (s, 2H), 4.41 (q, 2H), 3.03 (m, 1H), 1.39 (t, 3H), 1.16 (d, 6H). Calculated mass for C18H21N3O2, 311.16. Observed 334.1 (M+1).

Example 13

Biological Assays of Certain Compounds of the Invention

The compounds of the invention were tested in various biological assays. The results of these assays indicated that the compounds of the invention ameliorated dysregulated bioenergetics and are, thus, useful for treatment of degenerative diseases and disorders, such as retinal damage.

MTT Assay

The compound 3-(4,5-Dimethylthiazol-2-yl)-2,5-diphenyltetrazolium bromide (MTT) is a tetrazolium ion that is reduced to a blue formazan dye via several families of NAD(P)H-dependent oxidoreductases. Formation of the formazan dye from MTT or other related tetrazolium dyes are commonly used as a viability assay even though, in fact, the assay is a metabolic capacity assay. While it is true that dead cells cannot produce NAD(P)H, very sick cells in the throes of death can exhibit extremely high levels of metabolic capacity as they attempt to overcome stress and it is well known that the MTT and related assays report on the ability of cells to produce reducing equivalents, and not live-dead ratios (Sumantran 2011). As shown below, it was found that the MTT assay was a useful metabolic assay when linked to more specific bioenergetic assays.

In this assay, 661W or C6 cells were maintained in DMEM supplemented with 10% FBS. 100 µL of 70,000 cells/mL cells were seeded into each well of 96 well plates using DMEM supplemented with 5% FBS. Cells were then allowed to grow to confluency for 48 hours. The compounds of the invention were added in 2 µL media and calcium-ionophore A23187 was then added in 1 µL for a final concentration of 1 µM and after 24 h, 20 uL of 2 µg/mL MTT were added to each well and the cells were incubated for another 4 h after which 100 µL of 1% SDS in 0.01M aqueous HCl were added to each well and the plates were incubated overnight. Absorbance was measured at 640 and 570 nM (background correction). The 1 µM ionophore A23187 caused about 50% loss in MTT signal at 24 h. Protection was calculated as the increase in absorbance of treatment groups normalized to the vehicle control. As shown in Table 1, the compounds of the invention gave significant protection at low concentrations:

TABLE 1

| Example | MTT Protection (%, concentration) |
| --- | --- |
| 1 | 10.4%, 800 pM |
| 2 | 73.9%, 800 pM |
| 3 | 43.5%, 1 nM |
| 4 | 87%, 10 nM |
| 5 | 76.6%, 10 nM |
| 6 | 73.5%, 10 nM |
| 7 | 40%, 10 nM |
| 8 | 75.6%, 1 nM |
| 9 | 59%, 1 nM |
| 10 | 47.8%, 1 nM |
| 11 | 28.3%, 1 µM |
| 12 | 59.4%, 1 nM |

XF FCCP-Uncoupled Oxygen Consumption Rate Assay

The XF FCCP-uncoupled oxygen consumption rate assay assesses mitochondrial capacity by measuring cellular respiration. It was shown that the maximum FCCP-uncoupled oxygen consumption rate (OCR) was a good estimate of maximal mitochondrial capacity (Beeson 2010) and that IBMX treatment of 661W or C6 cells for 24 h caused a loss in maximal uncoupled OCR (Perron 2013). Thus, cells were pretreated with the exemplified compounds for 1 h, added 600 µM IBMX and then measured the uncoupled rate after 24 h. The OCR measurements were performed using a Seahorse Bioscience XF instrument (Seahorse Bioscience, Billerica, Md.), as previously published (Perron 2013). $O_2$ leakage through the plastic sides and bottom of the plate was accounted for using the AKOS algorithm in the XF software package. Cells were plated on 96- or 24-well custom plates designed for use in the XF and grown to confluency in DMEM+5% FBS (48 h). The medium was then replaced with DMEM+1% FBS for 24 h, along with any treatments. The IBMX treatment alone typically caused about a 50% decrease in the uncoupled rate and protection was calculated as the increase in absorbance of treatment groups normalized to the vehicle control. As shown in Table 2, below, the compounds of the invention gave significant protection in the concentration ranges that gave maximal protection in the MTT assay:

TABLE 2

| Example No. | XF FCCP OCR (% Ctrl, concentration) |
| --- | --- |
| 1 | 58% @ 1uM |
| 2 | 62% @ 100 nM |
| 3 | Not Tested |
| 4 | 67% @ 10 nM |
| 5 | 72% @ 10 nM |
| 6 | 75% @ 10 nM |
| 8 | 64% @ 100 nM |
| 9 | 67% @ 100 nM |

Retinal Degeneration Assay

The in vitro data demonstrated that the compounds of the invention mitigated oxidative- and calcium-induced loss of mitochondrial metabolic capacity. It was reasoned that the compounds' activities would enable them to protect against loss of photoreceptors in retinal degenerative animal models. As a translational bridge between the cell line-based assays and in vivo animal studies, mouse retina organ cultures were utilized. These retinal explants were a powerful ex vivo screening tool, which allowed the testing of photoreceptor cell survival within the retinal network, and the effects of a specific compound were tested like in an in vitro system, without systemic interference. In this assay, the rdl mouse was utilized. The genotype of the rdl mouse has a mutation in the β-subunit of the phosphodiesterase gene. This mutation resulted in high levels of cGMP, leaving an increased number of the cGMP-gated channels in the open state, allowing intracellular calcium to rise to toxic levels and rapid rod degeneration. The genetic deficit and the retinal pathology were very similar to that observed in the patients with βPDE-dependent RP. In these mice, rod photoreceptor degeneration started after postnatal day 10 (P10), progressing rapidly, such that at P21, only 1-2 rows of photoreceptor remained, mainly representing cones. Finally, the rdl mouse retina was amenable to culturing, replicating both retinal development and degeneration, following the same time course as in vivo. The retinal explants were cultured for 11 days ex vivo. Explants were treated with compounds of the invention. Additives were replaced with fresh medium in every alternate day. At the end of the experiments, tissues were fixed, sectioned and stained with 0.1% toluidine and the numbers of rows of photoreceptors remaining in the outer nuclear layer (ONL) were counted. Rd1 explants treated with vehicle only were found to contain 1.2±0.19 cells in the ONL. This was in contrast to cultures treated with the compounds of the invention that showed significant protection (Table 3 below):

TABLE 3

| Example No. | Rd1 vehicle (# of rows) | rd1 protection (concentration, # of rows) |
| --- | --- | --- |
| 2 | 1.3 | 20 nM 4.46 |
| 4 | 1.16 | 10 nM 3.2 |

Light Model Assay

The light model assay is generally accepted as a model of age related macular degeneration (AMD). Light as an environmental factor has been shown to be toxic to rod photoreceptors if the retina was exposed to high light levels over a long period of time; and oxidative stress has been implicated as the main trigger for cell death. In particular, oxidative damage has been detected by immunohistochemistry, detecting the presence of oxidized and tyrosine-phosphorylated proteins as well as the upregulation of endogenous antioxidants such as thioredoxin and glutathione peroxidase. Likewise, exogenous antioxidants have been found to protect the rodent retina from light damage. Additional indirect evidence for the involvement of oxidative stress in photoreceptor degeneration has been provided by treatment of photodamaged retinas with antioxidants such as dimethylthiourea, or the treatment of N-methyl-N-nitrosourea (MNU)-challenged rats with the antioxidant DHA.

The light model assay was used to further test the therapeutic potential of the compounds of the invention. Photoreceptors from albino animals are very sensitive to constant light, lacking the RPE pigment to protect them. Thus, Balb/c mice were exposed to continuous light for 7 days, which caused loss of about 50% of the photoreceptor cells as measured via histology. To test the potential therapeutic efficacy, eyedrops were formulated in 0.1% Bij 35 in 9% saline, applied once or twice daily throughout the period of light exposure, and assessed their effect on the light-induced degeneration of photoreceptor cells morphologically and electrophysiologically, 10 days after the onset of the CL exposure. In control BALB/c mice, constant light resulted in the elimination of ~50% of the photoreceptors (average retina score: 4.3±0.25 rows of photoreceptors), whereas the mice treated with compound eyedrops once per day retained significantly more photoreceptors cells (Table 4).

TABLE 4

| Example | LD vehicle (# of rows) | LD Protection (concentration, # of rows) |
|---|---|---|
| 4 | 4.95 | 125 µM 6.42 |

As seen above, the compounds of the invention mitigate oxidative- and calcium-mediated loss of mitochondrial capacity in cell lines and protect photoreceptors from cell death in several models of retinal degeneration.

REFERENCES

Acosta M L, Fletcher E L, Azizoglu S, Foster L E, Farber D B, Kalloniatis M: Early markers of retinal degeneration in rd/rd mice. Mol Vis 2005, 11:717-728.

Acosta M L, Shin Y S, Ready S, Fletcher E L, Christie D L, Kalloniatis M. Retinal metabolic state of the proline-23-histidine rat model of retinitis pigmentosa. Am J Physiol Cell Physiol. 2010 March; 298(3):C764-74. doi: 10.1152/ajpcell.00253.2009. Epub 2009 Dec. 23. PubMed PMID: 20032515.

Bandyopadhyay M, Rohrer B. Photoreceptor structure and function is maintained in organotypic cultures of mouse retinas. Mol Vis. 2010 Jun. 26; 16:1178-85. PubMed PMID: 20664685; PubMed Central PMCID: PMC2901185.

Barot M, Gokulgandhi M R, Mitra A K. Mitochondrial dysfunction in retinal diseases. Curr Eye Res. 2011 December; 36(12):1069-77. doi: 10.3109/02713683.2011.607536. Epub 2011 Oct. 6. Review. PubMed PMID: 21978133.

Beal D M, Jones L H. Molecular scaffolds using multiple orthogonal conjugations: applications in chemical biology and drug discovery. Angew Chem Int Ed Engl. 2012 Jun. 25; 51(26):6320-6. doi: 10.1002/anie.201200002. Epub 2012 Apr. 19. Review. PubMed PMID: 22517597.

Beeson C C, Beeson G C, Schnellmann R G. A high-throughput respirometric assay for mitochondrial biogenesis and toxicity. Anal Biochem. 2010 Sep. 1; 404(1):75-81. doi: 10.1016/j.ab.2010.04.040. Epub 2010 May 11. PubMed PMID: 20465991; PubMed Central PMCID: PMC2900494.

Booij J C, van Soest S, Swagemakers S M, Essing A H, Verkerk A J, van der Spek P J, Gorgels T G, Bergen A A. Functional annotation of the human retinal pigment epithelium transcriptome. BMC Genomics. 2009 Apr. 20; 10:164. doi: 10.1186/1471-2164-10-164. PubMed PMID: 19379482; PubMed Central PMCID: PMC2679759.

Bruce J E. In vivo protein complex topologies: sights through a cross-linking lens. Proteomics. 2012 May; 12(10): 1565-75. doi: 10.1002/pmic.201100516. Review. PubMed PMID: 22610688.

Catoire M, Mensink M, Boekschoten M V, Hangelbroek R, Müller M, Schrauwen P, Kersten S. Pronounced effects of acute endurance exercise on gene expression in resting and exercising human skeletal muscle. PLoS One. 2012; 7(11): e51066. doi: 10.1371/journal.pone.0051066. Epub 2012 Nov. 30. PubMed PMID: 23226462; PubMed Central PMCID: PMC3511348.

Cavalier-Smith T, Chao E E. Phylogeny of choanozoa, apusozoa, and other protozoa and early eukaryote megaevolution. J Mol Evol. 2003 May; 56(5):540-63. PubMed PMID: 12698292.

Cazares L H, Troyer D A, Wang B, Drake R R, Semmes O J. MALDI tissue imaging: from biomarker discovery to clinical applications. Anal Bioanal Chem. 2011 July; 401 (1):17-27. doi: 10.1007/s00216-011-5003-6. Epub 2011 May 4. Review. PubMed PMID: 21541816.

Chaurand P, Cornett D S, Caprioli R M. Molecular imaging of thin mammalian tissue sections by mass spectrometry. Curr Opin Biotechnol. 2006 August; 17(4):431-6. Epub 2006 Jun. 16. Review. PubMed PMID: 16781865.

Chen Y A, Almeida J S, Richards A J, Müller P, Carroll R J, Rohrer B. A nonparametric approach to detect nonlinear correlation in gene expression. J Comput Graph Stat. 2010 Sep. 1; 19(3):552-568. PubMed PMID: 20877445; PubMed Central PMCID: PMC2945392.

Copple I M. The Keap1-Nrf2 cell defense pathway—a promising therapeutic target Adv Pharmacol. 2012; 63:43-79. doi: 10.1016/B978-0-12-398339-8.00002-1. Review. PubMed PMID: 22776639.

Court F A, Coleman M P. Mitochondria as a central sensor for axonal degenerative stimuli. Trends Neurosci. 2012 June; 35(6):364-72. doi: 10.1016/j.tins.2012.04.001. Epub 2012 May 11. Review. PubMed PMID: 22578891.

Dai C, Cazares L H, Wang L, Chu Y, Wang S L, Troyer D A, Semmes O J, Drake R R, Wang B. Using boronolectin in MALDI-MS imaging for the histological analysis of cancer tissue expressing the sialyl Lewis X antigen. Chem Commun (Camb). 2011 Oct. 7; 47(37):10338-40. doi: 10.1039/c1cc11814e. Epub 2011 Aug. 19. PubMed PMID: 21853197.

Daiger S P, Sullivan L S, Bowne S J, Birch D G, Heckenlively J R, Pierce E A, Weinstock G M. Targeted high-throughput DNA sequencing for gene discovery in retinitis pigmentosa. Adv Exp Med Biol. 2010; 664:325-31. doi: 10.1007/978-1-4419-1399-9_37. PubMed PMID: 20238032; PubMed Central PMCID: PMC2909649.

De Jesús-Cortés H, X u P, Drawbridge J, Estill S J, Huntington P, Tran S, Britt J, Tesla R, Morlock L, Naidoo J, Melito L M, Wang G, Williams N S, Ready J M, McKnight S L, Pieper A A. Neuroprotective efficacy of aminopropyl carbazoles in a mouse model of Parkinson disease. Proc Natl Acad Sci USA. 2012 Oct. 16; 109(42):17010-5. doi: 10.1073/pnas.1213956109. Epub 2012 Oct. 1. PubMed PMID: 23027934; PubMed Central PMCID: PMC3479520.

Demos C, Bandyopadhyay M, Rohrer B. Identification of candidate genes for human retinal degeneration loci using differentially expressed genes from mouse photoreceptor dystrophy models. Mol Vis. 2008 Sep. 5; 14:1639-49. PubMed PMID: 18776951; PubMed Central PMCID: PMC2529471.

Dong S Q, Xu H Z, Xia X B, Wang S, Zhang L X, Liu S Z. Activation of the ERK 1/2 and STAT3 signaling pathways is required for 661W cell survival following oxidant injury. Int J Ophthalmol. 2012; 5(2):138-42. doi: 10.3980/j.issn.2222-3959.2012.02.04. Epub 2012 Apr. 18. PubMed PMID: 22762037; PubMed Central PMCID: PMC3359025.

Egger A, Samardzija M, Sothilingam V, Tanimoto N, Lange C, Salatino S, Fang L, Garcia-Garrido M, Beck S, Okoniewski M J, Neutzner A, Seeliger M W, Grimm C, Handschin C. PGC-1α determines light damage susceptibility of the murine retina. PLoS One. 2012; 7(2):e31272. doi: 10.1371/journal.pone.0031272. Epub 2012 Feb. 13. PubMed PMID: 22348062; PubMed Central PMCID: PMC3278422.

Estrada-Cuzcano A, Roepman R, Cremers F P, den Hollander A I, Mans D A. Non-syndromic retinal ciliopathies: translating gene discovery into therapy. Hum Mol Genet. 2012 Oct. 15; 21(R1):R111-24. Epub 2012 Jul. 26. PubMed PMID: 22843501.

Falk M J, Zhang Q, Nakamaru-Ogiso E, Kannabiran C, Fonseca-Kelly Z, Chakarova C, Audo I, Mackay D S, Zeitz C, Borman A D, Staniszewska M, Shukla R, Palavalli L, Mohand-Said S, Waseem N H, Jalali S, Perin J C, Place E, Ostrovsky J, Xiao R, Bhattacharya S S, Consugar M, Webster A R, Sahel J A, Moore A T, Berson E L, Liu Q, Gai X, Pierce E A. NMNAT1 mutations cause Leber congenital amaurosis. Nat Genet. 2012 September; 44(9):1040-5. doi: 10.1038/ng.2361. Epub 2012 Jul. 29. PubMed PMID: 22842227; PubMed Central PMCID: PMC3454532.

Farber D B, Lolley R N: Cyclic guanosine monophosphate: elevation in degenerating photoreceptor cells of the C3H mouse retina. Science 1974, 186:449-451.

Farber D B: From mice to men: the cyclic GMP phosphodiesterase gene in vision and disease. The Proctor Lecture. Invest Ophthalmol Vis Sci 1995, 36(2):263-275.

Ferrick D A, Neilson A, Beeson C. Advances in measuring cellular bioenergetics using extracellular flux. Drug Discov Today. 2008 March; 13(5-6):268-74. doi: 10.1016/j.drudis.2007.12.008. Epub 2008 Feb. 13. Review. PubMed PMID: 18342804.

Fox D A, Poblenz A T, He L: Calcium overload triggers rod photoreceptor apoptotic cell death in chemical-induced and inherited retinal degenerations. Ann NY Acad Sci 1999, 893:282-285.

Gilliam J C, Chang J T, Sandoval I M, Zhang Y, Li T, Pittler S J, Chiu W, Wensel T G. Three-dimensional architecture of the rod sensory cilium and its disruption in retinal neurodegeneration. Cell. 2012 Nov. 21; 151(5):1029-41. doi: 10.1016/j.cell.2012.10.038. PubMed PMID: 23178122.

Graymore C: Metabolism of the Developing Retina. 7. Lactic Dehydrogenase Isoenzyme in the Normal and Degenerating Retina. a Preliminary Communication. Exp Eye Res 1964, 89:5-8.

Hartong D T, Dange M, McGee T L, Berson E L, Dryja T P, Colman R F. Insights from retinitis pigmentosa into the roles of isocitrate dehydrogenases in the Krebs cycle. Nat Genet. 2008 October; 40(10):1230-4. doi: 10.1038/ng.223.

Epub 2008 Sep. 21. PubMed PMID: 18806796; PubMed Central PMCID: PMC2596605.

Ho C H, Piotrowski J, Dixon S J, Baryshnikova A, Costanzo M, Boone C. Combining functional genomics and chemical biology to identify targets of bioactive compounds. Curr Opin Chem Biol. 2011 February; 15(1):66-78. doi: 10.1016/j.cbpa.2010.10.023. Epub 2010 Nov. 17. Review. PubMed PMID: 21093351.

Ibebunjo C, Chick J M, Kendall T, Eash J K, Li C, Zhang Y, Vickers C, Wu Z, Clarke B A, Shi J, Cruz J, Fournier B, Brachat S, Gutzwiller S, Ma Q, Markovits J, Broome M, Steinkrauss M, Skuba E, Galarneau J R, Gygi S P, Glass D J. Genomic and proteomic profiling reveals reduced mitochondrial function and disruption of the neuromuscular junction driving rat sarcopenia. Mol Cell Biol. 2013 January; 33(2):194-212. doi: 10.1128/MCB.01036-12. Epub 2012 Oct. 29. PubMed PMID: 23109432.

Jaliffa C, Ameqrane I, Dansault A, Leemput J, Vieira V, Lacassagne E, Provost A, Bigot K, Masson C, Menasche M, Abitbol M. Sirt1 involvement in rd10 mouse retinal degeneration. Invest Ophthalmol Vis Sci. 2009 August; 50(8): 3562-72. doi: 10.1167/iovs.08-2817. Epub 2009 Apr. 30. PubMed PMID: 19407027.

Jarrett S G, Rohrer B, Perron N R, Beeson C, Boulton M E. Assessment of mitochondrial damage in retinal cells and tissues using quantitative polymerase chain reaction for mitochondrial DNA damage and extracellular flux assay for mitochondrial respiration activity. Methods Mol Biol. 2013; 935:227-43. doi: 10.1007/978-1-62703-080-9_16. PubMed PMID: 23150372.

Jewett J C, Bertozzi C R. Cu-free click cycloaddition reactions in chemical biology. Chem Soc Rev. 2010 April; 39(4):1272-9. Review. PubMed PMID: 20349533; PubMed Central PMCID: PMC2865253.

Kanan Y, Moiseyev G, Agarwal N, Ma J X, Al-Ubaidi M R. Light induces programmed cell death by activating multiple independent proteases in a cone photoreceptor cell line. Invest Ophthalmol Vis Sci. 2007 January; 48(1):40-51. PubMed PMID: 17197514.

Kandpal R P, Rajasimha H K, Brooks M J, Nellissery J, Wan J, Qian J, Kern T S, Swaroop A. Transcriptome analysis using next generation sequencing reveals molecular signatures of diabetic retinopathy and efficacy of candidate drugs. Mol Vis. 2012; 18:1123-46. Epub 2012 May 2. PubMed PMID: 22605924; PubMed Central PMCID: PMC3351417.

Karbowski M, Neutzner A. Neurodegeneration as a consequence of failed mitochondrial maintenance. Acta Neuropathol. 2012 Febuary; 123(2): 157-71. doi: 10.1007/s00401-011-0921-0. Epub 2011 Dec. 7. Review. PubMed PMID: 22143516.

Kroeger H, Messah C, Ahern K, Gee J, Joseph V, Matthes M T, Yasumura D, Gorbatyuk M S, Chiang W C, Lavail M M, Lin J H. Induction of Endoplasmic Reticulum Stress Genes, BiP and Chop, in Genetic and Environmental Models of Retinal Degeneration. Invest Ophthalmol Vis Sci. 2012 Nov. 9; 53(12):7590-9. doi: 10.1167/iovs.12-10221. PubMed PMID: 23074209; PubMed Central PMCID: PMC3495601.

Krysko D V, Agostinis P, Krysko O, Garg A D, Bachert C, Lambrecht B N, Vandenabeele P. Emerging role of damage-associated molecular patterns derived from mitochondria in inflammation. Trends Immunol. 2011 April; 32(4):157-64. doi: 10.1016/j.it.2011.01.005. Epub 2011 Feb. 19. Review. PubMed PMID: 21334975.

Kunchithapautham K, Rohrer B: Apoptosis and Autophagy in Photoreceptors Exposed to Oxidative Stress. Autophagy 2007, 3(5).

Lenz E M, Wilson I D: Analytical strategies in metabonomics. *J Proteome Res* 2007, 6(2):443-458.

Lin J H, Lavail M M. Misfolded proteins and retinal dystrophies. Adv Exp Med Biol. 2010; 664:115-21. doi: 10.1007/978-1-4419-1399-9_14. Review. PubMed PMID: 20238009; PubMed Central PMCID: PMC2955894.

Liu Q, Tan G, Levenkova N, Li T, Pugh E N Jr, Rux J J, Speicher D W, Pierce E A. The proteome of the mouse photoreceptor sensory cilium complex. Mol Cell Proteomics. 2007 August; 6(8):1299-317. Epub 2007 May 9. PubMed PMID: 17494944; PubMed Central PMCID: PMC2128741.

Liu Q, Zhang Q, Pierce E A. Photoreceptor sensory cilia and inherited retinal degeneration. Adv Exp Med Biol. 2010; 664:223-32. doi: 10.1007/978-1-4419-1399-9_26. Review. PubMed PMID: 20238021; PubMed Central PMCID: PMC2888132.

Lohr H R, Kuntchithapautham K, Sharma A K, Rohrer B: Multiple, parallel cellular suicide mechanisms participate in photoreceptor cell death. Exp Eye Res 2006, 83(2):380-389.

Lohr H R, Kuntchithapautham K, Sharma A K, Rohrer B. Multiple, parallel cellular suicide mechanisms participate in photoreceptor cell death. Exp Eye Res. 2006 August; 83(2): 380-9. Epub 2006 Apr. 19. Erratum in: Exp Eye Res. 2006 December; 83(6):1522. PubMed PMID: 16626700.

MacMillan K S, Naidoo J, Liang J, Melito L, Williams N S, Morlock L, Huntington P J, Estill S J, Longgood J, Becker G L, McKnight S L, Pieper A A, De Brabander J K, Ready J M. Development of proneurogenic, neuroprotective small molecules. J Am Chem Soc. 2011 Feb. 9; 133(5):1428-37. doi: 10.1021/ja108211m. Epub 2011 Jan. 6. PubMed PMID: 21210688; PubMed Central PMCID: PMC3033481.

Mamidyala S K, Finn M G. In situ click chemistry: probing the binding landscapes of biological molecules. Chem Soc Rev. 2010 April; 39(4):1252-61. doi: 10.1039/b901969n. Epub 2010 Mar. 1. Review. PubMed PMID: 20309485.

Mandal M N, Patlolla J M, Zheng L, Agbaga M P, Tran J T, Wicker L, Kasus-Jacobi A, Elliott M H, Rao C V, Anderson R E. Curcumin protects retinal cells from light- and oxidant stress-induced cell death. Free Radic Biol Med. 2009 Mar. 1; 46(5):672-9. doi: 10.1016/j.freeradbiomed.2008.12.006. Epub 2008 Dec. 24. PubMed PMID: 19121385; PubMed Central PMCID: PMC2810836.

Marina N, Sajic M, Bull N D, Hyatt A J, Berry D, Smith K J, Martin K R. Lamotrigine monotherapy does not provide protection against the loss of optic nerve axons in a rat model of ocular hypertension. Exp Eye Res. 2012 November; 104:1-6. doi: 10.1016/j.exer.2012.09.002. Epub 2012 Sep. 13. PubMed PMID: 22982756.

Mattson M P, Kroemer G: Mitochondria in cell death: novel targets for neuroprotection and cardioprotection. Trends Mol Med 2003, 9(5):196-205.

McKnight S L. Back to the future: molecular biology meets metabolism. Cold Spring Harb Symp Quant Biol. 2011; 76:403-11. doi: 10.1101/sqb.2012.76.013722. Epub 2012 Apr. 17. Review. PubMed PMID: 22510749.

Mueller E E, Schaier E, Brunner S M, Eder W, Mayr J A, Egger S F, Nischler C, Oberkofler H, Reitsamer H A, Patsch W, Sperl W, Kofler B. Mitochondrial haplogroups and control region polymorphisms in age-related macular degeneration: a case-control study. PLoS One. 2012; 7(2):e30874. doi: 10.1371/journal.pone.0030874. Epub 2012 Feb. 13. PubMed PMID: 22348027; PubMed Central PMCID: PMC3278404.

Mulkidjanian A Y, Galperin M Y, Makarova K S, Wolf Y I, Koonin E V. Evolutionary primacy of sodium bioenergetics. Biol Direct. 2008 Apr. 1; 3:13. doi: 10.1186/1745-6150-3-13. PubMed PMID: 18380897; PubMed Central PMCID: PMC2359735.

Nicholas P C, Kim D, Crews F T, Macdonald J M: (1)H NMR-Based Metabolomic Analysis of Liver, Serum, and Brain Following Ethanol Administration in Rats. *Chem Res Toxicol* 2007.

Nixon E, Simpkins J W. Neuroprotective effects of non-feminizing estrogens in retinal photoreceptor neurons. Invest Ophthalmol Vis Sci. 2012 Jul. 12; 53(8):4739-47. doi: 10.1167/iovs.12-9517. Print 2012 July PubMed PMID: 22700711.

O'Toole J F, Liu Y, Davis E E, Westlake C J, Attanasio M, Otto E A, Seelow D, Nurnberg G, Becker C, Nuutinen M, Kärppä M, Ignatius J, Uusimaa J, Pakanen S, Jaakkola E, van den Heuvel L P, Fehrenbach H, Wiggins R, Goyal M, Zhou W, Wolf M T, Wise E, Helou J, Allen S J, Murga-Zamalloa C A, Ashraf S, Chaki M, Heeringa S, Chernin G, Hoskins B E, Chaib H, Gleeson J, Kusakabe T, Suzuki T, Isaac R E, Quarmby L M, Tennant B, Fujioka H, Tuominen H, Hassinen I, Lohi H, van Houten J L, Rotig A, Sayer J A, Rolinski B, Freisinger P, Madhavan S M, Herzer M, Madignier F, Prokisch H, Nurnberg P, Jackson P K, Khanna H, Katsanis N, Hildebrandt F. Individuals with mutations in XPNPEP3, which encodes a mitochondrial protein, develop a nephronophthisis-like nephropathy. J Clin Invest. 2010 March; 120(3):791-802. doi: 10.1172/JCI40076. Epub 2010 Feb. 22. Erratum in: J Clin Invest. 2010 April; 120(4):1362. Jackson, Peter [corrected to Jackson, Peter K]. PubMed PMID: 20179356; PubMed Central PMCID: PMC2827951.

Osborne N N, Del Olmo-Aguado S. Maintenance of retinal ganglion cell mitochondrial functions as a neuroprotective strategy in glaucoma. Curr Opin Pharmacol. 2012 Sep. 19. doi:pii: 51471-4892(12)00159-2. 10.1016/j.coph.2012.09.002. [Epub ahead of print] PubMed PMID: 22999653.

Pappas D J, Gabatto P A, Oksenberg D, Khankhanian P, Baranzini S E, Gan L, Oksenberg J R. Transcriptional expression patterns triggered by chemically distinct neuroprotective molecules. Neuroscience. 2012 Dec. 13; 226:10-20. doi: 10.1016/j.neuroscience.2012.09.007. Epub 2012 Sep. 15. PubMed PMID: 22986168; PubMed Central PMCID: PMC3489981.

Pereira D A, Williams J A. Origin and evolution of high throughput screening. Br J Pharmacol. 2007 September; 152(1):53-61. Epub 2007 Jul. 2. Review. PubMed PMID: 17603542; PubMed Central PMCID: PMC1978279.

Perron N R, Beeson C, Rohrer B. Early alterations in mitochondrial reserve capacity; a means to predict subsequent photoreceptor cell death. J Bioenerg Biomembr. 2012 Oct. 23. [Epub ahead of print] PubMed PMID: 23090843.

Pieper A A, Xie S, Capota E, Estill S J, Zhong J, Long J M, Becker G L, Huntington P, Goldman S E, Shen C H, Capota M, Britt J K, Kotti T, Ure K, Brat D J, Williams N S, MacMillan K S, Naidoo J, Melito L, Hsieh J, De Brabander J, Ready J M, McKnight S L. Discovery of a proneurogenic, neuroprotective chemical. Cell. 2010 Jul. 9; 142(1):39-51. doi: 10.1016/j.cell.2010.06.018. PubMed PMID: 20603013; PubMed Central PMCID: PMC2930815.

Pierce E A, Quinn T, Meehan T, McGee T L, Berson E L, Dryja T P: Mutations in a gene encoding a new oxygen-regulated photoreceptor protein cause dominant retinitis pigmentosa. Nat Genet 1999, 22(3):248-254.

Pierce E A: Pathways to photoreceptor cell death in inherited retinal degenerations. Bioessays 2001, 23(7):605-618.

Qin L X, Beyer R P, Hudson F N, Linford N J, Morris D E, Kerr K F. Evaluation of methods for oligonucleotide array data via quantitative real-time PCR. BMC Bioinformatics. 2006 Jan. 17; 7:23. PubMed PMID: 16417622; PubMed Central PMCID: PMC1360686.

Rezaie T, McKercher S R, Kosaka K, Seki M, Wheeler L, Viswanath V, Chun T, Joshi R, Valencia M, Sasaki S, Tozawa T, Satoh T, Lipton S A. Protective effect of carnosic Acid, a pro-electrophilic compound, in models of oxidative stress and light-induced retinal degeneration. Invest Ophthalmol Vis Sci. 2012 Nov. 27; 53(12):7847-54. doi: 10.1167/iovs.12-10793. PubMed PMID: 23081978; PubMed Central PMCID: PMC3508754.

Richards A J, Muller B, Shotwell M, Cowart L A, Rohrer B, Lu X. Assessing the functional coherence of gene sets with metrics based on the Gene Ontology graph. Bioinformatics. 2010 Jun. 15; 26(12):i79-87. doi: 10.1093/bioinformatics/btq203. PubMed PMID: 20529941; PubMed Central PMCID: PMC2881388.

Richards T A, Cavalier-Smith T. Myosin domain evolution and the primary divergence of eukaryotes. Nature. 2005 Aug. 25; 436(7054):1113-8. PubMed PMID: 16121172.

Rohrer B, Matthes M T, LaVail M M, Reichardt L F: Lack of p75 receptor does not protect photoreceptors from light-induced cell death. *Exp Eye Res* 2003, 76(1):125-129

Rohrer B, Pinto F R, Hulse K E, Lohr H R, Zhang L, Almeida J S. Multidestructive pathways triggered in photoreceptor cell death of the rd mouse as determined through gene expression profiling. J Biol Chem. 2004 Oct. 1; 279 (40):41903-10. Epub 2004 Jun. 24. PubMed PMID: 15218024.

Ronquillo C C, Bernstein P S, Baehr W. Senior-Løken syndrome: A syndromic form of retinal dystrophy associated with nephronophthisis. Vision Res. 2012 Dec. 15; 75:88-97. doi: 10.1016/j.visres.2012.07.003. Epub 2012 Jul. 20. PubMed PMID: 22819833; PubMed Central PMCID: PMC3504181.

Sancho-Pelluz J, Alavi M V, Sahaboglu A, Kustermann S, Farinelli P, Azadi S, van Veen T, Romero F J, Paquet-Durand F, Ekström P. Excessive HDAC activation is critical for neurodegeneration in the rd1 mouse. Cell Death Dis. 2010; 1:e24. doi: 10.1038/cddis.2010.4. PubMed PMID: 21364632; PubMed Central PMCID: PMC3032332.

Sancho-Pelluz J, Arango-Gonzalez B, Kustermann S, Romero F J, van Veen T, Zrenner E, Ekström P, Paquet-Durand F. Photoreceptor cell death mechanisms in inherited retinal degeneration. Mol Neurobiol. 2008 December; 38(3): 253-69. doi: 10.1007/s12035-008-8045-9. Epub 2008 Nov. 4. Review. PubMed PMID: 18982459.

SanGiovanni J P, Arking D E, Iyengar S K, Elashoff M, Clemons T E, Reed G F, Henning A K, Sivakumaran T A, Xu X, DeWan A, Agrón E, Rochtchina E, Sue C M, Wang J J, Mitchell P, Hoh J, Francis P J, Klein M L, Chew E Y, Chakravarti A. Mitochondrial DNA variants of respiratory complex I that uniquely characterize haplogroup T2 are associated with increased risk of age-related macular degeneration. PLoS One. 2009; 4(5):e5508. doi: 10.1371/journal.pone.0005508. Epub 2009 May 12. PubMed PMID: 19434233; PubMed Central PMCID: PMC2677106.

Schrier S A, Falk M J. Mitochondrial disorders and the eye. Curr Opin Ophthalmol. 2011 September; 22(5):325-31. doi: 10.1097/ICU.0b013e328349419d. Review. PubMed PMID: 21730846.

Sharma A K, Rohrer B: Calcium-induced calpain mediates apoptosis via caspase-3 in a mouse photoreceptor cell line. J Biol Chem 2004, 279(34):35564-35572.

Sharma A K, Rohrer B. Calcium-induced calpain mediates apoptosis via caspase-3 in a mouse photoreceptor cell line. J Biol Chem. 2004 Aug. 20; 279(34):35564-72. Epub 2004 Jun. 18. PubMed PMID: 15208318.

Sharma A K, Rohrer B. Sustained elevation of intracellular cGMP causes oxidative stress triggering calpain-mediated apoptosis in photoreceptor degeneration. Curr Eye Res. 2007 March; 32(3):259-69. PubMed PMID: 17453946.

Shimazaki H, Hironaka K, Fujisawa T, Tsuruma K, Tozuka Y, Shimazawa M, Takeuchi H, Hara H. Edaravone-loaded liposome eyedrops protect against light-induced retinal damage in mice. Invest Ophthalmol Vis Sci. 2011 Sep. 21; 52(10):7289-97. doi: 10.1167/iovs.11-7983. Print 2011 September. PubMed PMID: 21849425.

Smith J J, Kenney R D, Gagne D J, Frushour B P, Ladd W, Galonek H L, Israelian K, Song J, Razvadauskaite G, Lynch A V, Carney D P, Johnson R J, Lavu S, Iffland A, Elliott P J, Lambert P D, Elliston K O, Jirousek M R, Milne J C, Boss O. Small molecule activators of SIRT1 replicate signaling pathways triggered by calorie restriction in vivo. BMC Syst Biol. 2009 Mar. 10; 3:31. doi: 10.1186/1752-0509-3-31. PubMed PMID: 19284563; PubMed Central PMCID: PMC2660283.

Spinazzi M, Cazzola S, Bortolozzi M, Baracca A, Loro E, Casarin A, Solaini G, Sgarbi G, Casalena G, Cenacchi G, Malena A, Frezza C, Carrara F, Angelini C, Scorrano L, Salviati L, Vergani L. A novel deletion in the GTPase domain of OPA1 causes defects in mitochondrial morphology and distribution, but not in function. Hum Mol Genet. 2008 Nov. 1; 17(21):3291-302. doi: 10.1093/hmg/ddn225. Epub 2008 Aug. 4. PubMed PMID: 18678599.

Stone J, Maslim J, Valter-Kocsi K, Mervin K, Bowers F, Chu Y, Barnett N, Provis J, Lewis G, Fisher S K et al: Mechanisms of photoreceptor death and survival in mammalian retina. Prog Retin Eye Res 1999, 18(6):689-735.

Sumantran V N. Cellular chemosensitivity assays: an overview. Methods Mol Biol. 2011; 731:219-36. doi: 10.1007/978-1-61779-080-5_19. Review. PubMed PMID: 21516411.

Tan E, Ding X Q, Saadi A, Agarwal N, Naash M I, Al-Ubaidi M R: Expression of cone-photoreceptor-specific antigens in a cell line derived from retinal tumors in transgenic mice. Invest Ophthalmol Vis Sci 2004, 45(3):764-768.

Tan E, Ding X Q, Saadi A, Agarwal N, Naash M I, Al-Ubaidi M R. Expression of cone-photoreceptor-specific antigens in a cell line derived from retinal tumors in transgenic mice. Invest Ophthalmol Vis Sci. 2004 March; 45(3): 764-8. PubMed PMID: 14985288; PubMed Central PMCID: PMC2937568.

Tesla R, Wolf H P, Xu P, Drawbridge J, Estill S J, Huntington P, McDaniel L, Knobbe W, Burket A, Tran S, Starwalt R, Morlock L, Naidoo J, Williams N S, Ready J M, McKnight S L, Pieper A A. Neuroprotective efficacy of aminopropyl carbazoles in a mouse model of amyotrophic lateral sclerosis. Proc. Natl. Acad. Sci USA. 2012 Oct. 16; 109(42):17016-21. doi: 10.1073/pnas.1213960109. Epub 2012 Oct. 1. PubMed PMID: 23027932; PubMed Central PMCID: PMC3479516.

Travis G H: Mechanisms of cell death in the inherited retinal degenerations. Am J Hum Genet 1998, 62(3):503-508.

Trifunović D, Sahaboglu A, Kaur J, Mend S, Zrenner E, Ueffing M, Arango-Gonzalez B, Paquet-Durand F. Neuroprotective strategies for the treatment of inherited photoreceptor degeneration. Curr Mol Med. 2012 June; 12(5):598-612. Review. PubMed PMID: 22515977.

Tu B P, Mohler R E, Liu J C, Dombek K M, Young E T, Synovec R E, McKnight S L. Cyclic changes in metabolic state during the life of a yeast cell. Proc Natl Acad Sci USA. 2007 Oct. 23; 104(43):16886-91. Epub 2007 Oct. 16. PubMed PMID: 17940006; PubMed Central PMCID: PMC2040445.

Van Bergen N J, Crowston J G, Kearns L S, Staffieri S E, Hewitt A W, Cohn A C, Mackey D A, Trounce I A. Mitochondrial oxidative phosphorylation compensation may preserve vision in patients with OPA1-linked autosomal dominant optic atrophy. PLoS One. 2011; 6(6):e2134. doi: 10.1371/journal.pone.0021347. Epub 2011 Jun. 22. PubMed PMID: 21731710; PubMed Central PMCID: PMC3120866.

Vingolo E M, De Mattia G, Giusti C, Forte R, Laurenti O, Pannarale M R: Treatment of nonproliferative diabetic retinopathy with Defibrotide in noninsulin-dependent diabetes mellitus: a pilot study. Acta Ophthalmol Scand 1999, 77(3): 315-320.

Wenzel A, Grimm C, Samardzija M, Reme C E: Molecular mechanisms of light-induced photoreceptor apoptosis and neuroprotection for retinal degeneration. Prog Retin Eye Res 2005, 24(2):275-306.

Whitfield J F, Chakravarthy B R. The neuronal primary cilium: driver of neurogenesis and memory formation in the hippocampal dentate gyrus Cell Signal. 2009 September; 21(9):1351-5. doi: 10.1016/j.cellsig.2009.02.013. Epub 2009 Feb. 26. Review. PubMed PMID: 19249355.

Winkler B S, Pourcho R G, Starnes C, Slocum J, Slocum N. Metabolic mapping in mammalian retina: a biochemical and 3H-2-deoxyglucose autoradiographic study. Exp Eye Res. 2003 September; 77(3):327-37. PubMed PMID: 12907165.

Winkler B S. Letter to the editor: Comments on retinal metabolic state in P23H and normal retinas. Am J Physiol Cell Physiol. 2010 July; 299(1):C185; author reply C186-7. doi: 10.1152/ajpcell.00109.2010. PubMed PMID: 20554913.

Yamada Y, Hidefumi K, Shion H, Oshikata M, Haramaki Y. Distribution of chloroquine in ocular tissue of pigmented rat using matrix-assisted laser desorption/ionization imaging quadrupole time-of-flight tandem mass spectrometry. Rapid Commun Mass Spectrom. 2011 Jun. 15; 25(11):1600-8. doi: 10.1002/rcm.5021. PubMed PMID: 21594935.

Yang L, Nyalwidhe J O, Guo S, Drake R R, Semmes O J. Targeted identification of metastasis-associated cell-surface sialoglycoproteins in prostate cancer. Mol Cell Proteomics. 2011 June; 10(6):M110.007294. doi: 10.1074/mcp.M110.007294. Epub 2011 Mar. 29. PubMed PMID: 21447706; PubMed Central PMCID: PMC3108840.

Ying W. NAD+ and NADH in cellular functions and cell death. Front Biosci. 2006 Sep. 1; 11:3129-48. Review. PubMed PMID: 16720381.

Farber, D. B., *From mice to men: the cyclic GMP phosphodiesterase gene in vision and disease. The Proctor Lecture.* Invest. Ophthalmol. Vis. Sci., 1995. 36(2): p. 263-275.

Farber, D. B. and R. N. Lolley, *Cyclic guanosine monophosphate: elevation in degenerating photoreceptor cells of the C3H mouse retina.* Science, 1974. 186: p. 449-451.

Fox, D. A., A. T. Poblenz, and L. He, *Calcium overload triggers rod photoreceptor apoptotic cell death in chemical-induced and inherited retinal degenerations.* Ann. N.Y. Acad. Sci., 1999. 893: p. 282-285.

Ogilvie, J. M., et al., *A reliable method for organ culture of neonatal mouse retina with long-term survival.* J. Neurosci. Methods, 1999. 87(1): p. 57-65.

It is to be understood that the invention is not limited to the particular embodiments of the invention described above, as variations of the particular embodiments may be made and still fall within the scope of the appended claims.

What is claimed is:

1. The compound according to formula (I):

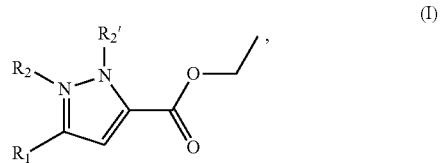

wherein:
R$_1$ is lower alkyl or trimethylsilyl;
one of R$_2$ or R$_{2'}$ is hydrogen and the other is —CH$_2$R$_3$ or —CH$_2$C(O)R$_3$; and
R$_3$ is 1H-indol-3-yl,
or a pharmaceutically acceptable salt thereof.

2. The compound according to claim 1, wherein R$_1$ is lower alkyl.

3. The compound according to claim 1, wherein R$_1$ is trimethylsilyl.

4. The compound according to claim 1, wherein one of R$_2$ or R$_{2'}$ is hydrogen and the other is —CH$_2$R$_3$.

5. The compound according to claim 1, wherein one of R$_2$ or R$_{2'}$ is hydrogen and the other is —CH$_2$C(O)R$_3$.

6. The compound according to claim 1, wherein said compound is:
Ethyl 1-((1H-indol-3-yl)methyl)-3-isopropyl-1H-pyrazole-5-carboxylate or a pharmaceutically acceptable salt thereof.

7. A pharmaceutical composition, comprising a therapeutically effective amount of a compound according to claim 1 or a pharmaceutically acceptable salt thereof and a pharmaceutically acceptable carrier.

* * * * *